United States Patent [19]

Engelbrecht

[11] Patent Number: 4,771,112

[45] Date of Patent: Sep. 13, 1988

[54] COMPOUNDS THAT CONSIST OF ALDEHYDE, EPOXIDE, ISOCYANATE, OR HALOTRIAZINE GROUPS, OF POLYMERIZABLE GROUPS, AND OF A HIGHER-MOLECULAR BACKBONE, MIXTURES THAT CONTAIN THEM, AND THE USE THEREOF

[75] Inventor: Jürgen Engelbrecht, Hamburg, Fed. Rep. of Germany

[73] Assignee: Ernst Muhlbauer KG, Hamburg, Fed. Rep. of Germany

[21] Appl. No.: 106,086

[22] Filed: Oct. 7, 1987

[30] Foreign Application Priority Data

Oct. 8, 1986 [DE] Fed. Rep. of Germany ....... 3634354

[51] Int. Cl.$^4$ .............................................. C08G 18/62
[52] U.S. Cl. ................................ 525/327.3; 427/386; 427/389; 427/389.9; 525/328.2; 525/328.4; 525/328.5; 525/328.7; 526/238.2; 526/238.21; 526/238.22; 526/261; 526/273; 526/301; 526/310; 526/315; 526/316; 528/73; 528/75; 528/96; 528/101; 528/220; 528/246

[58] Field of Search ............... 525/327.3, 328.2, 328.4, 525/328.5, 328.7; 526/238.2, 238.21, 238.22, 261, 273, 301, 310, 315, 316; 528/73, 75, 96, 101, 220, 246; 427/386, 388.2, 389, 389.9

[56] References Cited

U.S. PATENT DOCUMENTS 4,203,220  5/1980  Cranfield ............................. 526/248

Primary Examiner—Maurice J. Welsh
Attorney, Agent, or Firm—Sprung Horn Kramer & Woods

[57] ABSTRACT

Oligomeric and prepolymeric organic compounds with aldehyde, epoxide, isocyanate, or halotriazine groups and polymerizable groups. Compounds of this type and mixtures thereof have outstanding adhesion properties, especially in relation to biological substrates, can be copolymerized with composites based on unsaturated monomers, and are especially appropriate in dentistry and medicine as adhesion promoters, adhesive fillers, or adhesive cement.

19 Claims, No Drawings

COMPOUNDS THAT CONSIST OF ALDEHYDE, EPOXIDE, ISOCYANATE, OR HALOTRIAZINE GROUPS, OF POLYMERIZABLE GROUPS, AND OF A HIGHER-MOLECULAR BACKBONE, MIXTURES THAT CONTAIN THEM, AND THE USE THEREOF

The invention relates to compounds that consist of aldehyde, epoxide, isocyanate, or halotriazine groups, or polymerizable groups, and of a higher-molecular backbone, to mixtures that contain them, and to the use thereof.

Compounds of this type adhere to various substrates, especially biological substrates. They can be used for general purposes, but can especially in the dental and medical fields be employed or added as components of polymerizable adhesion promoters, adhesive fillers, adhesive cements, and similar mixtures.

Polymerizable mixtures based on monomers of compounds with one or more unsaturated groups are the basis of a number of plastics, the compounds with methacrylate groups being important in dentistry and medicine in particular. Mixtures of this type are the basis for plastic filling and sealing materials.

These polymerizable mixtures, however, cannot enter into chemical compounds with other materials, especially biological substrates, even when the substrates contain sufficient unpolymerized polymerizable groups.

A secure bond can accordingly be achieved only to highly retentive surfaces, by means, that is, of a strictly mechanical connection, by etching the surface of the biological or inorganic materials for example. This drawback can of course be eliminated by using adhesion promoters, substrates, that is, that react chemically with biological or inorganic materials and that have a polymerizable group.

A series of adhesion promoters are known—the organosilanes with their vinyl or methacryl groups for example. Their adhesive action, however, is limited to silicon dioxide, glasses that contain silicon dioxide, ceramics, and metal oxides or non-precious metals that form such oxides. They do not adhere to biological substrates, especially dental tissue or bone, but actually have a separating tendency in relation thereto.

A series of polymerizable adhesion promoters with other adhesive groups has been discovered for substrates of this type. These substances—benzaldehyde methacrylate (J. M. Antonucci, J. Dent. Res. 57, 500 [1978]), combinations of dialdehydes and hydroxyalkyl methacrylates (Eur. Pat. No. 0 141 324), epoxyalkyl methacrylates, isocyanoalkyl methacrylates, combinations of diisocyanates with methacrylates that contain hydroxy or amino groups, and allyl halotriazines (U.S. Pat. No. 4,203,220)—react to advantage with the collagen or collagen-like constituents of the substrates. There are also several polymerizable compounds that react with the apatite compounds in the dental tissue or bone. These adhesion promoters have acid groups or reactive acid-group derivatives. Some examples of these polymerizable groups are unsaturated organic esters of phosphoric or phosphonic acids (German AS No. 2 711 234 & German OS No. 3,150,285), unsaturated organic esters of monofluorophosphatic acid (U.S. Pat. No. 3,997,504), unsaturated organic esters of phosphoric acid that contain chlorine or bromine bonded directly to the phosphorus (Eur. Pat. No. 0 058 483), unsaturated organic esters of phosphoric acid in the form of cyclic pyrophosphates (anhydrides) (German OS No. 3 048 410), and unsaturated carboxylic acids and reactive derivatives thereof, such as 4-methacryloyloxyethyltrimellitic acid and its anhydride (Iakeyama, M. et al., I. Jap. Soc. f. Dent. App. a. Mat. 19, 179]1978] and bis-2-methacryloylethyl pyromellitate.

These polymerizable compounds result in many cases in a more or less powerful adhesion of the polymerizable filling and sealing materials to the dental tissue or bone. Successful use, however, also depends extensively on how thick a layer of the adhesion promoter is applied and on how many adhesive groups react with the biological substrate and how many polymerizable groups react with the copolymerizing material.

German Patent Application P No. 3 536 077 (Englebrecht et al.) describes oligomeric and prepolymeric compounds that contain several polymerizable groups and several adhesive groups bonded to an oligomeric or prepolymeric backbone. The adhesive groups are acid groups or reactive derivatives thereof.

Compounds of this type have several polymerizable and adhesive groups and accordingly exhibit a considerably higher adhesive force than do the corresponding monomeric compounds.

The additional incorporation of aldehyde, epoxide, isocyanate, or halotriazine groups into these polymerizable oligomers and prepolymers that contain acid groups could increase adhesion, especially to the dentin, even more. These groups, which are introduced into the higher-molecular compounds especially to promote bonding to collagen-like substrates, are, however, not always compatible with the acid groups or their reactive derivatives because the acid groups block off many amino polymerization initiators.

The object of the present invention is accordingly to provide compounds that have several adhesive groups in the form of aldehyde, epoxide, isocyanate or halotriazine groups, that have several polymerizable groups, and that do not have any acid groups or reactive derivatives thereof.

This object is attained in accordance with the invention by providing oligomeric or prepolymeric organic compounds that consist of chemically highly stable molecular backbones, several polymerizable groups, and several aldehyde, epoxide, isocyanate, or halotriazine groups.

It has been discovered that compounds of this type can be obtained by preparing oligomeric or prepolymeric backbones in the form of homo- or co-oligomers or homo- or copolymers that contain the desired aldehyde, epoxide, isocyanate, or halotriazine groups and can be grafted onto the polymerizable groups or that contain functional groups that both the desired aldehyde, epoxide, isocyanate, or halotriazine groups and polymerizable groups can be tied to.

The compounds in accordance with the invention contain in a practical way three or more polymerizable unsaturated groups and three or more aldehyde, epoxide, isocyanate, or halotriazine groups. Thus, depending on the substrate that the compound is supposed to adhere to or on the polymerizable mixture that contains them, there will be more polymerizable groups than adhesive groups, more adhesive groups than polymerizable groups, or the same number of adhesive and polymerizable groups.

Appropriate polymerizable unsaturated groups are all alkenyl, alkenoxy, cycloalkenyl, aralkenyl, and alkenaryl groups, with the acryl, methacryl, vinyl, and styryl groups preferred and the acryl and methacryl groups, which constitute the polymerizable groups of many monomers in dental materials, especially preferred.

The aldehyde, epoxide, isocyanate, or halotriazine groups can be bonded to the higher-molecular backbone directly or through an aliphatic, aromatic, or heterocyclic group.

The aldehyde groups can be formyl groups, acetaldehyde groups, vanillin, salicylaldehyde, O-phthalaldehyde, anisaldehyde, furfural, etc. They can also be acetals or semiacetals.

The epoxide groups can be components of the higher-molecular backbone

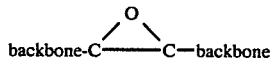

or be attached in the form of an epoxyglycidyl or epoxypropoxyphenyl group.

They can also be a nitrogen analog, specifically an epamine that reacts and adheres like the epoxides. They can also be present in the form of a three-component $CNC_1$ or CNN ring.

The isocyanate groups are bonded to the backbone either directly or in the form of isocyanatophenyl or isocyanatoethyl esters.

The halotriazine groups can be bonded to the backbone either directly or though an aminoalkyl, hydroxyalkyl, or aniline group.

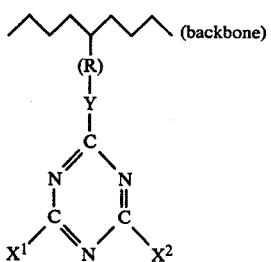

wherein
R is either no group or any group,
$X^1$ and $X^2$ are F, Cl, or Br, and
Y=NR′ or O, with R′ being H or alkyl.

The oligomeric or polymer backbones can be linear, branched, or cyclic.

They can be polymers of ethylenically unsaturated monomers or such oligomeric or polymeric compounds for example as polyesters, polyamides, polyethers, polyphosphazenes, polysaccharides, etc. if their structure is sufficiently hydrolysis stable and does not itself react with the adhesive groups. The backbones can contain the adhesive groups even while they are forming, although other functional groups that allow the adhesive groups to be grafted on and the polymerizable groups to be tied on later can also be used.

Preferred backbones are polymers of ethylenically unsaturated monomers.

Either a group of monomers that leads to homo-oligomers or homopolymers or a group that leads, by combining different monomers, to co-oligomers or copolymers is appropriate. Appropriate members of the group of homopolymers for example are (A) such oligomers or polymers of unsaturated aldehyde, epoxide, isocyanate, or halotriazine compounds as vinyl formaldehyde, styryl aldehyde, vanillin, epoxyglycidyl methacrylate, styryl isocyanate, allylamino dichlorotriazine etc.:

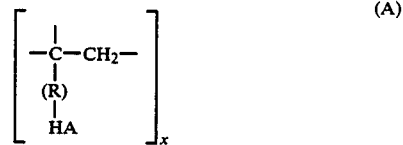

wherein
R is any inert group and
HA are adhesive groups: aldehyde, epoxide, isocyanate, or halotriazine.

They can then be treated to some extent in a second stage with polymerizable groups by reacting them for example with hydroxyalkylmethacrylates into (B), (C), or (D):

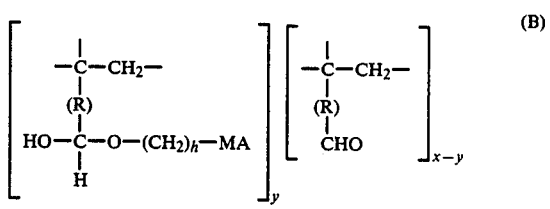

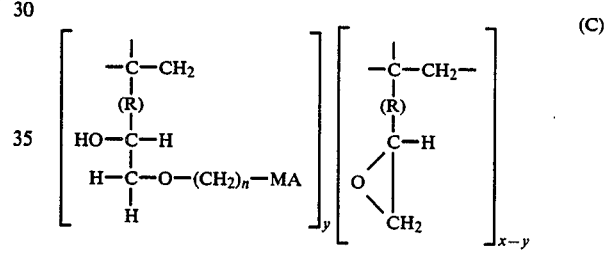

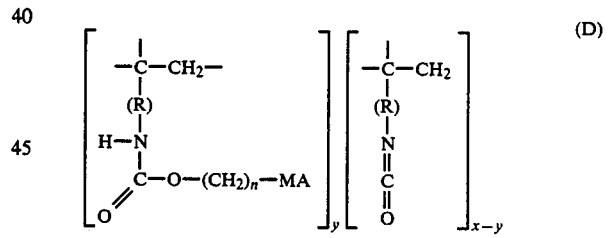

wherein MA represents the methacryl group

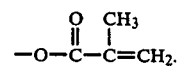

It is on the other hand also possible to provide for example a polyisocyanate with aldehyde groups by treating it to some extent with aminoalkylaldehyde and then with methacryl groups by treating it to some extent with hydroxyalkyl methacrylate to obtain for example a polymethacrylated polybutyral aldehyde.

The polyisocyanate can for example also be initially reacted to some extent with epoxypropanol and the residual isocyanate groups converted into polymethacrylated polyglycidylepoxide with hydroxyalkylmethacrylate.

The group of co-oligomers and copolymers includes (E) and (F), co-oligomers and copolymers of for example unsaturated isocyanates with unsaturated epoxides or unsaturated halotriazine compounds:

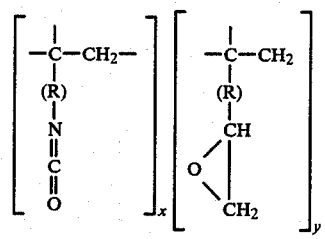
(E)

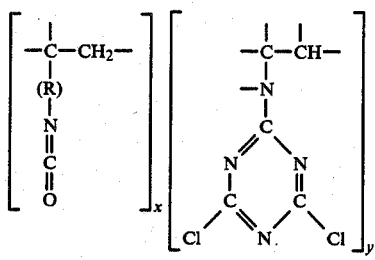
(F)

Compounds of this type can then for example be partly methacrylated through the more reactive group with a hydroxyalkylmethacrylate, resulting in such compounds in accordance with the invention as (G) and (H):

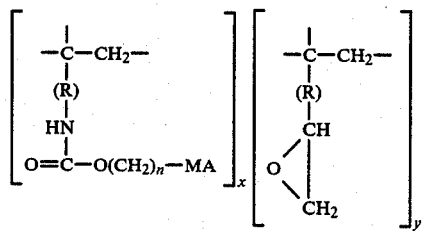
(G)

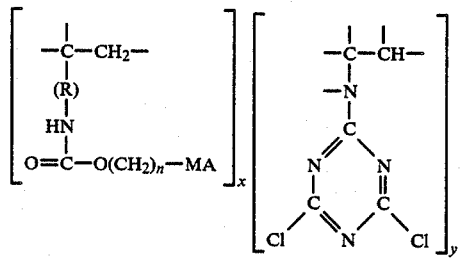
(H)

Units that do not contain aldehyde, epoxide, isocyanate, or halotriazine groups or a polymerizable group can also be polymerized in while the backbone is being constructed. It can for example be useful to vary the solubility in this way as for example during the incorporation of inert methylmethacrylate units (I):

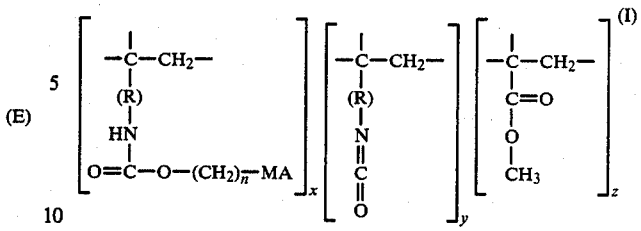
(I)

The incorporation of units with groups that can be parts of a polymerization-catalyst system can also be practical, although the groups do not absolutely have to be present as such during the homo- or copolymerization of the backbone but can also be tied on later to an isocyanate group.

How the reaction that leads to the fundamental oligomeric or prepolymeric compounds proceeds can be controlled by selecting different solvents, solubilities, concentrations, temperatures, and polymerization catalysts in ways that are known to one of skill in the art.

It can be important to ensure that the polymerization catalysts employed are destroyed by the reaction and that any residues are eliminated before the polymerizable groups in accordance with the invention are introduced.

The oligomeric compounds in accordance with the invention advantageously have a molecular weight that is higher than 500, and the prepolymeric compounds a molecular weight that is advantageously higher than 1500, preferably no higher than 100 000, and especially preferably no higher than 20 000.

The compounds in accordance with the invention can be employed by themselves, but will preferably be mixed with other polymerizable compounds.

The mixtures can also contain polymerizable unsaturated monomers, oligomers, or polymers that do not have any aldehyde, epoxide, isocyanate, or halotriazine groups. Especially appropriate are monomers that are components of conventional polymerizable composites and of polymerizable dental-resin mixtures and do not contain any alcohol groups—triethyleneglycol dimethacrylate or ethoxylated bisphenol-A dimethacrylate for instance.

The mixtures can also contain admixtures of other compounds with aldehyde, epoxide, isocyanate, or halotriazine groups.

Adding compounds that can, in addition to cross-linkage through radical polymerization of the unsaturated groups, lead to parallel cross-linkage of aldehyde, epoxide, isocyanate, or halotriazine groups can also be practical. Compounds of this type include polyols, polyamines, polyamides, and proteins. A "dual" curing of this type can indicate an intersecting modification that can lead to adhesion not only to very polar substrates—if there are enough polyols, polyamines, polyamides, or proteins—even in an aqueous medium but also—in cross-linking systems on this basis—to adhesion to such radically polymerizing systems as for example composites based on a (meth)acrylate.

It can also be helpful to add a highly volatile inert solvent to ensure that the mixture can be applied in a very thin coating to the structure that it is to adhere to.

Polymerization catalysts can be added to cure the mixture. Appropriate in principle are all systems that can trigger radical polymerization of olefinic compounds. Polyaddition or polycondensation catalysts can also be added to obtain dual curing.

It is in this context not essential whether the catalysis is initiated by heat, by adding an activator to react the catalyst, or by radiation with light. What is important, however, is for the catalyst system to dissolve readily enough in the mixture and essentially not be inhibited or destroyed by the compounds in accordance with the invention.

Healing components like cortisone or corticoids, neatsfoot oil, etc. can also be added if indicated for strictly medical reasons. Compounds that donate fluoride, such as for instance sodium fluorophosphate or aminofluorides, can also be added for similar reasons.

The mixtures containing the compound in accordance with the invention can also be treated with optionally surface-treated organic or inorganic fillers, whereby the inorganic filler can derive from the group of powdered quartz, microfine silicic acid, aluminum oxide, barium glasses, and other (inert) mineral substances conventional in composites, silanized if at all possible, as well as from the group of such finely ground fillers as powdered metal hydroxides, metal oxides, glasses and ceramics, zeolites, non-precious metals, apatite, etc. conventional in cements.

The compounds in accordance with the invention are new, and their properties can easily be varied by varying the ratio of the polymerizable groups to the adhesive aldehyde, epoxide, isocyanate, or halotriazine groups or by selecting the size of the molecules.

Many compounds with outstanding adhesive properties can be prepared.

They can, alone or in mixtures with other polymerizable compounds, be extended with many different fillers, resulting, subsequent to curing, in materials that are very strong and will adhere to a wide range of substrates. Even with only 1 to 10% of the compounds in accordance with the invention, the polymerizable mixtures, whether extended or not, will exhibit, subsequent to polymerization, a definite adhesive action or improved adhesion to many, especially biological, substrates along with a very secure bond to composites when they are polymerized just ahead of time or polymerized on shortly after.

The compounds in accordance with the invention can be employed to prepare more reliable adhesive mixtures that will adhere better to dental tissue or bone in particular with bonds that are longer lasting and more secure as well as filling and sealing materials that can be used with the mixtures and adhesives that can be used between them.

The compounds in accordance with the invention and the polymerizable mixtures thereof can accordingly be very helpful as effective dentin, enamel, or bone adhesives, as sealants for enamel, cracks, or tooth-neck defects, as adhesive protective lacquers for oversensitive tooth necks, as root-canal filling materials, cavity liners, or crown and bridge cements, as cements for orthodontic purposes, and also as bone cements.

Although the description of the invention has been essentially confined herein to use on dental tissue or bone and in particular to reaction with the components of those substances that contain collagen as well as to plastics that are polymers of monomers with unsaturated groups, the invention can also be employed in other fields. This is especially true of its application to human, animal, and plant tissues and to such products of animal or plant tissues as leather for example. It can furthermore be applied to oxidic, mineral, ceramic, vitreous, and metal substrates and to a wide range of plastic products to the extent that they or at least their surfaces react with the aldehyde, epoxide, isocyanate, or halotriazine groups or result, due to improve crosslinkage, in a definite adhesive action.

This is especially true of surfaces coated for example with epoxides or polyurethanes and of surfaces treated for example with natural, modified, or synthetic bioadhesives based on proteins, including even such systems that adhere under water as for example "muscle glues."

The potential for working fillers, pigments, and fibers into polymerizable mixtures can also be increased by means of the compounds in accordance with the invention to the extent that a surface reaction occurs or crosslinkage is improved, and will lead to greater strength on the part of the polymerized mixtures.

Cured mixtures are also promising as new materials for castings or coatings over inorganic or organic fillers, pigments, and fibers. Their surfaces will exhibit aldehyde, epoxide, isocyanate, or halotriazine groups that are still reactive, although no longer polymerizable, and accordingly capable of chemical bonding.

The invention will now be described with reference to examples. Unless otherwise specified, proportions and percentages are by weight.

EXAMPLE 1

Preparation of polymethacrylated polyvinyl formal 4.5 g of polyvinyl formal (Ega-Chemie) are treated with 2.5 g of hydroxyethyl methacrylate in 40 ml of tetrahydrofuran. The hydroxyethyl methacrylate reacts completely in 4 weeks.

The tetrahydrofuran is removed, leaving polymethacrylated polyvinyl formal in the form of a highly viscous brown oil.

EXAMPLE 2

Preparing a photocuring dentin-adhesion agent

A Mixture I is prepared from

| | |
|---|---|
| 55 parts | bisphenol-A glycidyl dimethacrylate (bis-GMA) |
| 45 | triethylene glycol dimethacrylate (TEDMA) |
| 2 | polymethacrylated polyvinyl formal (from Ex. 1) |
| 0.3 | camphorquinone and |
| 0.3 | butyldimethyl aniline. |

A similar reference mixture (II) was prepared without the polymethacrylated polyvinyl formal.

Both mixtures cured under halogen light in 10 seconds.

Adhesion was tested on a freshly polished bovine-dentin surface. Several teeth were prepared by brushing on two coatings of the mixture (I) in accordance with the invention and of the reference mixture (II) and curing them for 10 seconds. Cylinders (4 mm in diameter and 6 mm high) of the filling material Composite Merz, photocuring (Merz, Germany) were then polymerized onto them.

The samples were left in water for 24 hours at 37° C. Retention was tested with a commercially available tensileforce testing machine.

| | |
|---|---|
| Adhesive Mixture I: | 7.3 N/mm$^2$ |

| -continued | |
|---|---|
| Adhesive Mixture II: | 0.4 N/mm² |

Another reference mixture in which the polymethacrylated polyvinyl formal was replaced with the same proportion (2 parts) of hydroxybenzaldehyde methacrylate exhibited a retention to bovine dentin of only 1.8 N/mm² when tested in the same way.

EXAMPLE 3

Preparing polymethacrylated polystyryl isocyanate 10.5 g of poly(methylene[polyphenyl isocyanate]) (Aldrich Chemical Co.) with a molecular weight of 360 were treated with 10.5 g of hydroxyethyl methacrylate and stirred. The intensity of the N=C=O band in the IR spectrum was, at 2265 cm$^{-1}$, definitely lower 24 hours later, and chromatography revealed no hydroxyethyl methacrylate. The resulting rather reddish and ropy oil turned out to be polymethacrylated polystyryl isocyanate.

EXAMPLE 4

Preparing a two-component mixture that adheres well to the teeth

An activator component is prepared from

| 55 parts | ethoxylated bisphenol-A dimethacrylate (bis-EMA) |
|---|---|
| 45 | TEDMA |
| 2 | butyldimethyl aniline and |
| 10 | polymethacrylated polystyryl isocyanate (Ex. 3). |

A catalyst component is prepared from

| 55 parts | bis-GMA |
|---|---|
| 45 | TEDMA |
| 1 | benzenyl peroxide and |
| 0.04 | butylated hydroxytoluene. |

A mixture of equal parts of these components cures in 1 minute. Bovine-tooth samples involving both the dentin and the enamel are prepared for retention testing as described with reference to Example 2, and Composite Merz cured on them. Retention was tested as described after leaving the samples in water for 24 hours at 37° C.

| Retention on dentin: | 8.9 N/mm² |
|---|---|
| Retention on enamel: | 13.4 N/mm² |

EXAMPLE 5

Preparing a photocuring glue

A photocuring mixture is prepared from

| 100 parts | bis-EMA |
|---|---|
| 100 | TEDMA |
| 100 | polymethacrylated polystyryl isocyanate (Ex. 3) |
| 1 | camphorquinone and |
| 1 | butyldimethylaniline(p-t-butyl-N,N—dimethyl-aniline) |

Samples of gold, non-precious metal (Resilloy), and porcelain were ground, polished, and washed with acetone. Two thin layers of the photocuring glue were applied to the metal surfaces and cured with cylinders of Composite Merz, photocuring. Retention was tested 2 hours later.

| Gold: | 4.7 N/mm² |
|---|---|
| Non-precious metal: | 11.5 N/mm² |
| Porcelain: | 18.0 N/mm² |

EXAMPLE 6

Primer for a brace adhesive

A primer (activator component) is prepared from

| 45 parts | bis-EMA |
|---|---|
| 37 | TEDMA |
| 10 | methacrylated polystyrene isocyanate (Ex. 3) and |
| 2 | butyldimethylaniline |

Metal orthodontic braces (with grid retainers) were thinly coated with the primer in accordance with the invention and with the primer employed with Right-On No-Mix Adhesive (TP Laboratories, USA). Bovine enamel was also coated with the primer in accordance with the invention and with the Right-On primer.

The catalyst-component paste was then positioned between the enamel and metal, and the structures in accordance with the invention and the commercially available structures pressed firmly together for 40 seconds. All the samples hardened and stuck together rapidly.

The braces were pulled off of the enamel 2 hours later. The samples with the primer in accordance with the invention separated between the metal and the adhesive, and the Right-On samples between the tooth and the adhesive.

It will be understood that the specification and examples are illustrative but not limitative of the present invention and that other embodiments within the spirit and scope of the invention will suggest themselves to those skilled in the art.

What is claimed is:

1. An oligomeric or prepolymeric organic compound that contains
   (a) several polymerizable unsaturated groups and
   (b) several aldehyde, epoxide, isocyanate or halotriazine groups, on (c) an oligomeric or prepolymeric backbone.

2. A compound according to claim 1, containing at least three polymerizable unsaturated groups and at least three aldehyde, epoxide, isocyanate or halotriazine groups.

3. A compound according to claim 1, wherein the polymerizable unsaturated groups comprise at least one of acrylic, methacrylic, vinyl and styryl groups; the aldehyde group if present is in the form of an acetal or semiacetal; the epoxide group if present is in the form of an epimine; the halotriazine group if present is a 4,6-dichlor-1,3,5-triazine group; and the oligomeric or prepolymeric backbone (c) is a homo- or co-polymer of an ethylenically unsaturated monomer or is a polyester, polyamide, polyether, polysulfone, polyphosphazene, or polysaccharide.

4. A compound according to claim 1, wherein it has a molecular weight of 500 to 100,000.

5. A compound according to claim 1, wherein it has a molecular weight of 1,500 to 20,000.

6. A compound according to claim 1, wherein it is poly(meth-)acrylated polyvinylformal.

7. A compound according to claim 1, wherein it is poly(meth-)acrylated polystyrylurethanglycidylepoxide.

8. A compound according to claim 1, wherein it is poly(meth-)acrylated polystyrylisocyanate.

9. A compound according to claim 1, wherein it is poly(meth-)acrylated polyallylaminodichlortriazine.

10. A polymerizable mixture containing at least one compound according to claim 1.

11. A polymerizable mixture comprising at least one compound according to claim 1 and one or more polymerizable unsaturated compounds or a compound with an aldehyde, epoxide, isocyanate, or halotriazine group.

12. A polymerizable mixture according to claim 11, further containing at least one polyol, polyamine, polyamide or protein which is able to crosslink ingredients of the mixture which contain aldehyde-, epoxide-, isocyanate- or halotriazine groups.

13. A polymerizable mixture according to claim 11, further containing at least one of a solvent, a polymerization-, polyaddition- or polycondensation catalyst, and a surface-treated or untreated inorganic or organic filler.

14. A method for repairing, filling, veneering or lining an oxidic, mineral, vitreous, ceramic, metallic, or biological substrate, comprising applying to said substrate a mixture according to claim 11, and causing that mixture to harden.

15. A method for adhering (a) an oxidic, mineral, vitreous, ceramic, metallic, or biological substrate to (b) an oxidic, mineral, vitreous, ceramic, metallic, biological, or acrylic substrate, comprising the steps of
(c) applying to said substrate (a) a mixture according to claim 11;
(d) bringing the substrate (b) into good contact with said substrate (a) and
(e) causing that composition to harden.

16. A method according to claim 15, wherein said substrate is hard dental tissue or bone, or is an acrylic substrate made by polymerization of monomers with unsaturated groups or by polyaddition or polycondensation of compounds with aldehyde, isocyanate, epoxide or halotriazine with polyols, polyamine, polyamide or proteins.

17. A method comprising coating inorganic or organic filler particles, pigments or fibers with a thin film of uncured mixtures according to claim 11, and then compounding said filler particles, pigments or fibers with a polymerizable binder resin to create a better bond between said filler particles, pigments or fibers to said polymerizable binder resin.

18. A method comprising coating filler particles, pigments or fibers comprising applying thereto a thin film of a polymerizable mixture according to claim 11 and curing said mixture, thereby altering the surface of said filler particles, pigments or fibers.

19. A method for producing a shaped object comprising molding a mixture according to claim 10, and causing said mixture to harden.

* * * * *